United States Patent
Law et al.

(10) Patent No.: US 10,499,792 B2
(45) Date of Patent: Dec. 10, 2019

(54) PHONE ADAPTER FOR FLEXIBLE LARYNGOSCOPE AND RIGID ENDOSCOPES

(71) Applicant: University of Washington, Seattle, WA (US)

(72) Inventors: Anthony Law, Seattle, WA (US); Angelique Berens, Seattle, WA (US); Muneaki Miyasaka, Seattle, WA (US); Randall Bly, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 237 days.

(21) Appl. No.: 15/470,609

(22) Filed: Mar. 27, 2017

(65) Prior Publication Data

US 2017/0273539 A1 Sep. 28, 2017

Related U.S. Application Data

(60) Provisional application No. 62/313,541, filed on Mar. 25, 2016.

(51) Int. Cl.
| | | |
|---|---|---|
| *A61B 1/00* | (2006.01) | |
| *H04N 5/225* | (2006.01) | |
| *A61B 1/04* | (2006.01) | |

(52) U.S. Cl.
CPC ............ *A61B 1/00* (2013.01); *A61B 1/00002* (2013.01); *A61B 1/00045* (2013.01); *A61B 1/00048* (2013.01); *A61B 1/04* (2013.01); *H04N 2005/2255* (2013.01)

(58) Field of Classification Search
CPC ... A61B 1/00; A61B 1/00002; A61B 1/00048; H04N 2005/2255
See application file for complete search history.

(56) References Cited

U.S. PATENT DOCUMENTS

| | | | |
|---|---|---|---|
| 5,879,289 A | 3/1999 | Yarush et al. | |
| 2008/0207996 A1 | 8/2008 | Tsai | |
| 2014/0051923 A1* | 2/2014 | Mirza et al. ....... | A61B 1/00126 600/103 |
| 2014/0142390 A1 | 5/2014 | Bromwich | |
| 2015/0112144 A1* | 4/2015 | Chen ................. | A61B 1/00167 600/156 |
| 2017/0273539 A1* | 9/2017 | Law ........................ | A61B 1/00 |
| 2018/0020932 A1* | 1/2018 | Chen ................... | A61B 5/0261 600/479 |

FOREIGN PATENT DOCUMENTS

WO     2014073950     5/2014

OTHER PUBLICATIONS

Wu et al., "An Innovative Smartphone-Based Otorhinoendoscope and Its Application in Mobile Health and Teleotolaryngology," J. Med. Internet Res., vol. 16, No. 3, Mar. 3, 2014, 16 pages.

* cited by examiner

*Primary Examiner* — Tsion B Owens
(74) *Attorney, Agent, or Firm* — Kilpatrick Townsend & Stockton LLP (57) ABSTRACT

An adapter for endoscopy can operably connect camera features and light source features of a portable electronic device with a respective viewfinder and illumination element of a medical endoscope. Systems including an endoscope, adapter, and handheld electronic device with a microphone, light source, and camera can, when connected, be used to perform stroboscopic endoscopic examinations.

21 Claims, 7 Drawing Sheets

PHONE ADAPTER FOR FLEXIBLE LARYNGOSCOPE AND RIGID ENDOSCOPES

CROSS-REFERENCES TO RELATED APPLICATIONS

The present application claims the benefit under 35 USC § 119(e) of U.S. Provisional Appln. No. 62/313,541 filed Mar. 25, 2016; the full disclosure which is incorporated herein by reference in its entirety for all purposes.

BACKGROUND OF THE INVENTION

Voice disorders are one of the most common complaints seen in otolaryngology clinics and have led to laryngeal endoscopy becoming an essential aspect of the physical exam. Since its inception in 1834, indirect laryngoscopy has necessitated three essential elements: a 'scope' for viewing distal features; a visualization portal; and an illumination source. Each of these elements has seen dramatic improvement, and now endoscopy is a sensitive and reliable means of diagnosis of laryngeal pathology.

Exams are no longer limited to rigid scopes, as fiberoptics allow for flexible transnasal examination of the larynx. Visualization can be completed with the aid of high-definition cameras instead of solely by the naked eye. And finally, endoscopic evaluations can now be illuminated using various light sources including, for example, halogen, xenon, and LED lights. One particular procedure, laryngeal stroboscopy, has been shown to improve diagnostic accuracy by about 17-34%. Stroboscopy gives the illusion of a slowed mucosal wave, thus allowing for a more detailed inspection. In conjunction with a deeper understanding of laryngeal anatomy and physiology, stroboscopy has increased the ability to detect lesions earlier in their presentation. In summation, these advances have given improved, diagnostics, therapeutic, and surgical planning capabilities of otolaryngologists. However, stroboscopy suffers from a high upfront investment cost.

Despite dramatic advances in laryngeal endoscopic techniques, access to exams (in particular stroboscopic exams) has been limited. Most current systems necessitate a 'tower' comprised of a desktop computer for file storage and analysis, a light source (e.g., halogen or xenon lamps), a voice-recording system, a strobe system, speakers, and other components. While there are variations of these traditional systems, all typically require the traditional electronics tower, which carries a high cost, may be physically immobile or ponderous (weighing up to 100 lbs), and may be fragile. Thus, conventional equipment needs for laryngeal endoscopic techniques may present a high technical barrier to widespread use.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Various embodiments herein described relate to apparatuses, systems, and methods for conducting endoscopy using an electronic device. Specific embodiments relate to modular apparatuses and systems for connecting an endoscopic device to an electronic device, and for conducting endoscopic procedures. Further embodiments relate to apparatuses, systems, and methods for conducting video laryngoscopy with stroboscopy.

BRIEF DESCRIPTION OF THE DRAWINGS

Various embodiments in accordance with the present disclosure will be described with reference to the drawings, in which.

DETAILED DESCRIPTION OF THE INVENTION

Endoscopic procedures, such as laryngoscopy, rely on obtaining an unobstructed and well illuminated view of tissues within a cavity of the body. Endoscopic procedures as discussed herein may refer to any such procedure. One exemplary procedure for which the procedures discussed herein is useful is laryngoscopy, in which an imaging device and a light source are inserted into the body to view the larynx. In specific procedures, such as flexible transnasal laryngoscopy (which may be referred to as fiberoptic laryngoscopy, fiberoptic flexible endoscopy, nasopharyngoscopy, or transnasal laryngoscopy), a light source and a light capturing element are inserted into the patient via the nasal cavity and positioned to simultaneously view and illuminate the vocal folds. Laryngeal stroboscopy, (also referred to as videostroboscopy, laryngostroboscopy, laryngo-videostroboscopy, stroboscopic laryngoscopy, or strobolaryngoscopy) is a technique whereby the lighting element transmits high-speed, strobing illumination of the vocal folds while the light capturing element captures an image of the vocal folds.

Apparatuses, systems, and methods described herein provide for the adaptation of endoscopic and stroboscopic techniques to a mobile device platform, wherein a portable electronic device (such as a smartphone or other mobile device, tablet, or comparable device) obviates the need for the large, and often expensive, accessory subunits required for endoscopic procedures. In recent years, portable electronic devices, such as smartphones, have become increasingly popular. These devices typically include a plethora of sensors, cameras, and lights. For example, embodiments herein disclosed include adapters for a portable electronic device which serves to couple an illumination port and a viewing port of an endoscope to onboard camera and illumination (light source) elements, respectively, of the portable electronic device. Through the combination of hardware and associated software an integrated portable-electronic-device-based endoscopy system can be used for any of, or any combination of: static and stroboscopic illumination, video capture, voice capture, data storage, and data analysis on the portable electronic device platform.

Using the light source of a portable electronic device offers multiple advantages over both the traditional large, halogen-based illumination systems and newer lightweight, LED-based illumination accessories. Compared to traditional halogen-based systems, light sources of portable electronic devices are smaller, cheaper, and typically need replacement less often. Further, the near ubiquitous nature of portable electronic devices obviates the need for additional equipment and increases speed and ease of the exam. Compared to current LED accessories, light sources from portable electronic devices, such as a smartphone-based LED illumination system, offer the ability for rapid cycling between the off/on state, thereby effectively creating a strobing mechanism suitable for stroboscopy.

In at least some embodiments, software operating on a portable electronic device can be used in conjunction with the aforementioned hardware to capture a patient's vocal sounds and analyze their fundamental frequency, in order to deliver strobed light to the endoscope in proximity to the fundamental voice frequency, thereby effectively providing an illumination pattern suitable for clinical stroboscopy.

Figure 1:
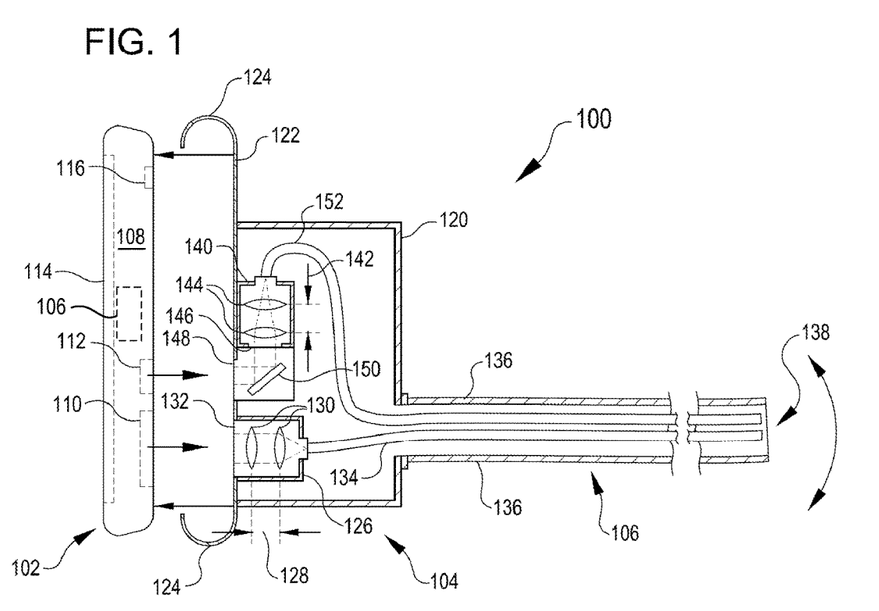
FIG. 1 is a cross-sectional schematic view illustrating an example of an endoscope for conducing endoscopy using an electronic device.

FIG. 1 is a simplified, cross-sectional schematic view illustrating an example of an assembly 100 that includes an endoscope 104 adapted to connect with and use an electronic device 102 for conducing endoscopic examinations, in accordance with embodiments. The electronic device can be, for example, a smart phone, a digital tablet, a hand held computer, or any other hand held electronic device having features as needed to meet one or more of the requirements set forth herein. Features herein are described with reference to a particular electronic device 102 and its components and configuration, but aspects of embodiments herein can be adapted to fit additional electronic devices. In the embodiment shown in FIG. 1, the electronic device 102 is defined by a device body 108 that includes a camera 110, a light source 112, a screen 114, and a microphone 116. The device body 108 can contain various processing and/or management elements at, e.g., a management component 106 (see FIG. 7). The camera 110 can be an HD camera, and may also be operable to take slow-motion video (e.g., up to 120 fps, or more).

The endoscope 104 includes an endoscope body or frame 120 connected with a light guide tube 106. An end 138 of the light guide tube 106 is configured for placement into an endocavity of a patient by a physician during an endoscopic examination. The light guide tube 106 contains a light source fiberoptic element 152 and a light receiving fiberoptic element 134 bundled inside a guide tube wall 136. Each fiberoptic element 152, 134 can be a bundle of fiberoptic elements. In particular, the light receiving fiberoptic element 134 is operable to transfer an image viewed at the light guide tube end 138. The light guide tube end 138 can optionally include further optics to enhance light capture by the light receiving fiberoptic element 134, to improve illumination efficacy by the light source fiberoptic element 152, or both. According to some embodiments, the endoscope 104 is a flexible endoscope, and may be suitable for procedures such as flexible transnasal laryngoscopy. According to some alternative embodiments, the endoscope 104 can be a rigid endoscope.

The endoscope 104 is configured to interface with a handheld electronic device, such as the handheld electronic device 102. The endoscope body 120 is connected with attachment element 122 including attachment features 124 which can wrap and either slidingly fit around the electronic device 102, deform to snap-fit over the device, or attach via other comparable means. An camera aperture 132 in the endoscope body 120 is positioned to align with the camera 110 of the electronic device 102, and a light receiving aperture 148 is positioned to align with the light source 112. In some embodiments, the microphone 116 may be acoustically unobstructed to receive environmental sounds, such as patient speech.

The camera aperture 132 is connected with an image optical element 126 that focuses an image from the light receiving fiberoptic element 134. The image optical element 126 includes one or more internal optics 130 for focusing or magnifying an image. For example, the internal optics 130 can be adjusted, e.g. by adjusting a distance 128 between optics, to achieve a telescopic effect and magnify a received image. In at least some embodiments, the optics 130 include a spherical lens that magnifies the image and maintains optical clarity. The image optical element 126 receives an image from the light receiving fiberoptic element 124, enhances the image, and provides the enhanced image for view by the camera 110 of the electronic device 102. In some embodiments, the camera aperture 132 can be irised or otherwise adjustable in size or shape in order to match the camera 110.

The light source aperture 148 is positioned to align with the light source 112 when the endoscope is connected with the electronic device 102. As can be understood, the light source aperture may have to be arranged in a different location for a different electronic device. A mirror 150 inside the endoscope body 120 is positioned to redirect light from the light source to a light source optical element 140. The light source optical element 140 can receive the light from the light source 112 via an internal aperture 148, focus the light via one or more optics 144, and direct the light into a the light source fiberoptic element 152. Depending on the properties of light from the light source 112, the light may be focused by adjusting the light source optics 144, e.g. adjusting a distance 142 between the optics.

In some alternative embodiments, e.g. where the camera 110 and light source 112 are spread apart, the mirror 150 may be omitted, such that the image optical element 126 and light source optical element 140 may be positioned in parallel. In various other embodiments, one or both of the image optical element 126 and light source optical element 140 may be positioned in different orientations using mirrors to direct light to and from the apertures 132, 148. Generally, where the camera 110 and light source 112 are placed close together on the electronic device 102, at least one of the apertures 132, 148 will employ one or more mirrors to direct light.

The endoscope 104 can be used with a suitable electronic device 102 in which the positions of the camera 110 and light source 112 match a position of camera and light source apertures 132, 148 of the endoscope 104. In operation, the endoscope 104 can be positioned over the electronic device 102, and the light guide tube 106 can be placed in position to perform an endoscopic examination.

The assembly 100 illustrates a modular endoscope 104 that can attach to a portable electronic device 102. However, the principles discussed above with respect to the modular endoscope 104 may be applied to modular systems that connect a portable electronic device with an endoscope via an intervening adapter.

Figure 2:
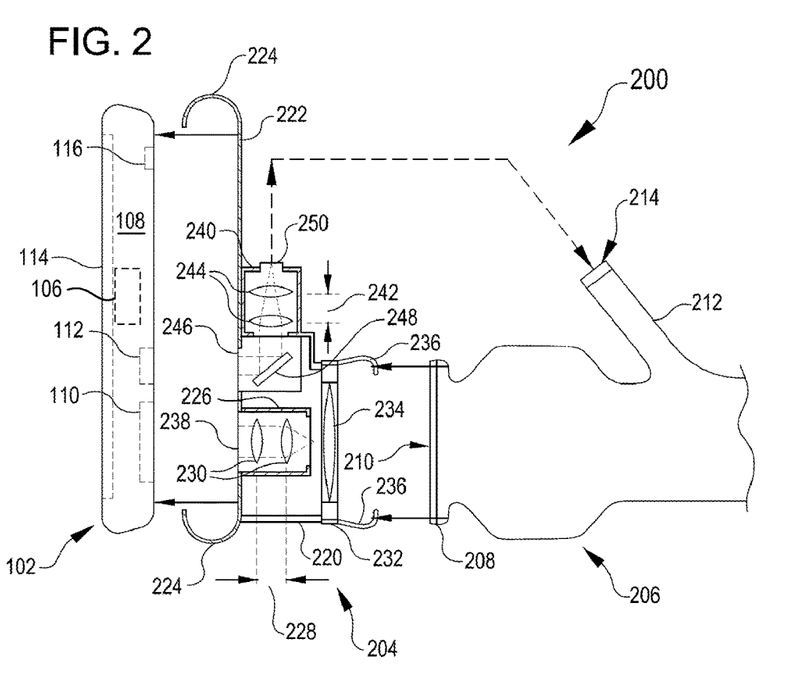
FIG. 2 is a cross-sectional schematic view illustrating an example of an adapter for conducting endoscopy with an endoscope and an electronic device.

FIG. 2 is a cross-sectional schematic view illustrating an example endoscopy system 200 including an adapter 204 for conducting endoscopy with an endoscope 206 and the electronic device 102 of FIG. 1, in accordance with embodiments. The electronic device 102 is defined by a device body 108 that includes a camera 110, a light source 112, a screen 114, and a microphone 116; and can contain a management component 106. The adapter 204 is configured to fit between the electronic device 102 and the endoscope 206. The endoscope 206 has a viewfinder 210 in a viewing portion 208 and an illumination element 212, to which any suitable source of illumination can be attached via a port 214. The endoscope 206 is representative of a medical endoscope, and may have additional features or a different configuration than that shown herein. According to some embodiments, the endoscope 204 is a flexible endoscope, and may be suitable for procedures such as flexible transnasal laryngoscopy. However, principles described herein as applied to flexible endoscopes may, in alternative embodiments, be applied to rigid endoscopes.

The adapter 204 has a body or frame 220 with first connecting features 224 for connecting the adapter with the electronic device 102, and with second connecting features 236 for connecting the adapter with the endoscope 206, and specifically with a viewfinder 210 in a viewing portion 208 of the endoscope. The first and second connecting features 224, 236 can include clips, hooks, a bracket for slidingly connecting to the electronic device 102 or endoscope 206, magnetic attachment features, or other comparable attachment features. The adapter 204, when narrowed than the electronic device 102, may include an extension 222 that positions the first attachment features 224 for connecting with the electronic device. In some cases, the extension 222 can extend along the electronic device 102 (i.e. in the out-of-plane direction) to cover or protect the electronic device from fluid or contaminants.

The body 220 of the adapter 204 contains a camera optical element 226 that is aligned with a camera aperture 238 of the adapter to provide light to the camera 110 of the electronic device 102. The camera aperture 238 can have features similar to those of the camera aperture 132 (FIG. 1), e.g., an adjustable or irised opening to restrict light to the camera, or features for blocking out ambient light. The camera optical element 226 is preferably aligned with a receiving optic 234 that aligns with the endoscope 206, so that light incident into the adapter from the endoscope is passed through the camera optical element and to the camera 110. Similar to the camera optical element 126 of FIG. 1, camera optical element 226 includes internal optics 230 that can be adjusted (e.g. by adjusting a distance 228 between the optics) for magnifying a received image while maintaining optical clarity. In some cases, the optics 230 includes a spherical lens to magnify the image. The receiving optic 234 that connects with the endoscope 206 is positioned in a receiving element 232 that connects with the body 220 of the adapter 204, and includes the second connecting features 236 for interfacing with the endoscope viewing portion 208.

The body 220 of the adapter 204 also contains a light source optical element 240 that is operably connected with a light source 112 of the electronic device 102. As shown, the light source optical element 240 can receive light passed from the light source 112 through a light source aperture 246 and via a mirror 148. The mirror 148 can include one more multiple elements for directing light to the light source optical element 240. In some alternative embodiments, the light source optical element 240 can be placed in-line with the light source aperture 246, or may be positioned in parallel with the camera optical element 226. The light source optical element 240 focuses and directs light to an light source output element 250, which can be a fiberoptic element or the like, for directing light to the port 214 of the illumination element 212 of the endoscope 206.

Thus, the adapter 204 shown in FIG. 2 is operable both to transfer light from the light source 112 of the electronic device 102 into the endoscope 206 for illuminating an endocavity; and to transfer light in the form of an image from the endoscope, via the viewfinder 210 and the adapter, to the camera 110 of the device. However, in other embodiments, illumination may be provided by additional light sources beyond the light source 110 of the electronic device 102; or may be provided via a different pathway, e.g., through the viewfinder 210.

Figure 3:
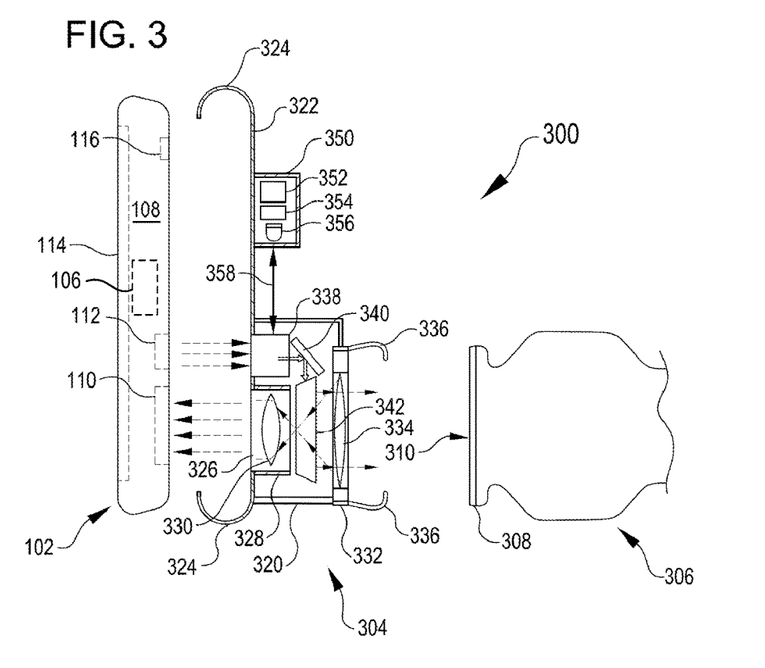
FIG. 3 is a cross-sectional schematic view illustrating a second example of an adapter for conducting endoscopy with an endoscope and an electronic device.

FIG. 3 is a cross-sectional schematic view illustrating a second example endoscopy system 300 including an adapter 304 for conducting endoscopy with an endoscope 306 and the electronic device 102 shown in FIG. 1, in accordance with embodiments. In the system 300, an adapter 304 is connected with the electronic device 102 of FIG. 1. The electronic device 102 is defined by a device body 108 that includes a camera 110, a light source 112, a screen 114, and a microphone 116; and can contain a management component 106. The adapter 304 is configured to fit between the electronic device 102 and the endoscope 306. The endoscope 306 has a viewfinder 310 in a viewing portion 308 which both transfers an image for viewing, and through which light can be passed in both directions. The endoscope 306 is representative of a medical endoscope, and may have additional features or a different configuration than that shown herein.

The adapter 304 has a body or frame 320 with first connecting features 324 for connecting the adapter with the electronic device 102, and with second connecting features 336 for connecting the adapter with the endoscope 306, and specifically with a viewing portion 308 of the endoscope. The first and second connecting features 324, 336 can include clips, hooks, a bracket for slidingly connecting to the electronic device 102 or endoscope 306, magnetic attachment features, or other comparable attachment features. The adapter 304, when narrowed than the electronic device 102, may include an extension 322 that positions the first attachment features 324 for connecting with the electronic device. In some cases, the extension 322 can extend along the electronic device 102 (i.e. in the out-of-plane direction) to cover or protect the electronic device from fluid or contaminants.

The body 320 of the adapter 304 contains a camera optical element 328 that is aligned with a camera aperture 326 of the adapter to provide light to the camera 110 of the electronic device 102. The camera aperture 326 can have features similar to those of the camera aperture 132 (FIG. 1), e.g., an adjustable or irised opening to restrict light to the camera, or features for blocking out ambient light. The camera optical element 328 is preferably aligned with a receiving optic 334 that aligns with the endoscope 306, so that light incident into the adapter from the endoscope is passed through the camera optical element and to the camera 110. Similar to the camera optical element 126 of FIG. 1, camera optical element 328 includes internal optics 330 that can be adjusted for magnifying a received image while maintaining optical clarity. In some cases, the optics 330 includes a spherical lens to magnify the image. The receiving optic 334 that connects with the endoscope 306 is positioned in a receiving element 332 that connects with the body 320 of the adapter 304, and includes the second connecting features 336 for interfacing with the viewfinder 310 in the viewing portion 308.

The body 320 of the adapter 304 also includes a light source optical element 338, which can contain internal optics for focusing and redirecting incident light from the light source 112 and/or light sensors for detecting light incident from the light source. In some embodiments, the light source optical element 338 directs focused light from the light source 112 via one or more mirrors 340 to a light ring 342 or comparable light directing element for directing light outward to the viewfinder 310 of the endoscope 306. In some embodiments, a secondary light source 350 can be operably connected with the light source optical element 338 for providing additional light for use in the endoscope 306 when incident light is detected at the light source optical element 338. The secondary light source 350 can include an independent power supply 352, electronics 354 for detecting a signal from the light source optical element 338, and a light-producing element 356 such as an LED or the like. Light produced by the secondary light source 350 can be combined with light from the light source 112, e.g. by a light collimator, can be passed through the light source optical element 338 to the light ring 342, or can be passed directly to the light ring. In alternative embodiments, the light ring 342 can include one or more additional light sources, such as LEDs, that are activated in response to the light source optical element 338 receiving light from the light source 112.

Figure 4:
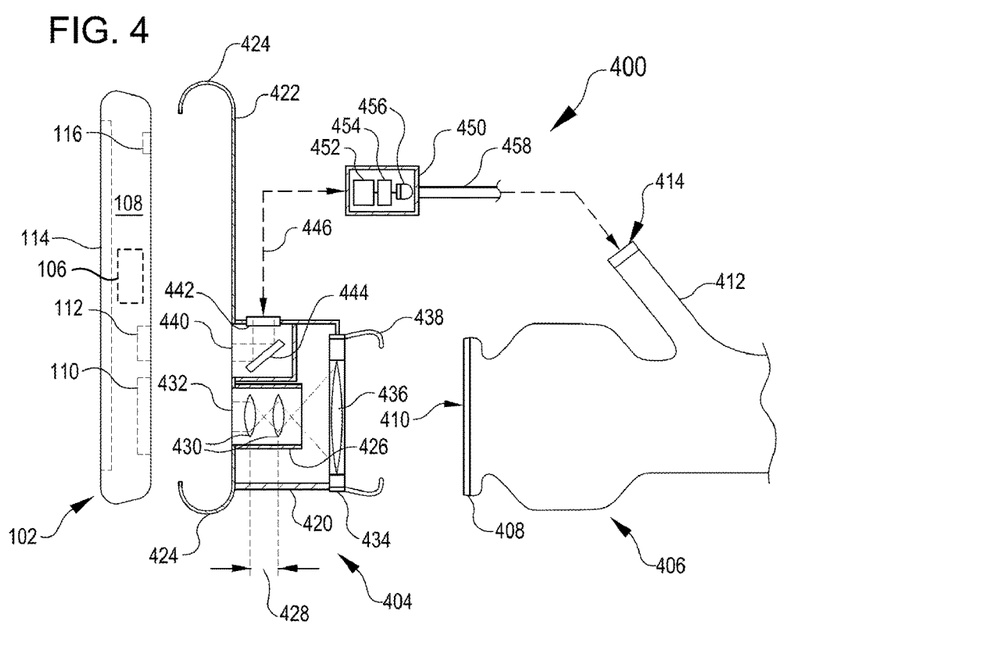
FIG. 4 is a cross-sectional schematic view illustrating a third example of an adapter for conducting endoscopy with an endoscope and an electronic device.

In some embodiments, the light source 112 may be used to activate a separate, secondary light source for providing illumination in the endoscope. For example, FIG. 4 is a cross-sectional schematic view illustrating a third example endoscopy system 400 including an adapter 404 for conducting endoscopy with an endoscope 406 and the electronic device 102 shown in FIG. 1, in accordance with embodiments.

Similar to adapters 204, 304 described above with respect to FIGS. 2 and 3, the adapter 404 has first connecting features 424 for connecting the adapter with an electronic device 102, and second connecting features 438 for connecting the adapter with an endoscope 406. The electronic device 102, similar to electronic devices described above, can include a device body 108 that includes a camera 110, a light source 112, a screen 114, and a microphone 116; and can contain a management component 106. The adapter 304 is configured to fit between the electronic device 102 and the endoscope 406. The endoscope 406 has a viewfinder 410 in a viewing portion 408, and an illumination element 412, to which any suitable source of illumination can be attached via a port 414. The endoscope 406 is representative of a medical endoscope, and may have additional features or a different configuration than that shown herein.

The adapter 404 has a body or frame 420 with first connecting features 424 for connecting the adapter with the electronic device 102, and with second connecting features 438 for connecting the adapter with the endoscope 406, and specifically with a viewfinder 410 in a viewing portion 408 of the endoscope. The first and second connecting features 424, 436 can include clips, hooks, a bracket for slidingly connecting to the electronic device 102 or endoscope 406, magnetic attachment features, or other comparable attachment features. The adapter 404, when narrowed than the electronic device 102, may include an extension 422 that positions the first attachment features 424 for connecting with the electronic device. In some cases, the extension 422 can extend along the electronic device 102 (i.e. in the out-of-plane direction) to cover or protect the electronic device from fluid or contaminants.

The body 420 of the adapter 404 contains a camera optical element 426 that is aligned with a camera aperture 432 of the adapter to provide light to the camera 110 of the electronic device 102. The camera aperture 432 can have features similar to those of the camera aperture 132 (FIG. 1), e.g., an adjustable or irised opening to restrict light to the camera, or features for blocking out ambient light. The camera optical element 426 is preferably aligned with a receiving optic 436 that aligns with the endoscope 406, so that light incident into the adapter from the endoscope is passed through the camera optical element and to the camera 110. Similar to the camera optical element 126 of FIG. 1, camera optical element 426 includes internal optics 430 that can be adjusted (e.g. by adjusting a distance 428 between the optics) for magnifying a received image while maintaining optical clarity. In some cases, the optics 430 include a spherical lens to magnify the image. The receiving optic 436 that connects with the endoscope 406 is positioned in a receiving element 434 that connects with the body 420 of the adapter 404, and includes the second connecting features 438 for interfacing with the endoscope viewing portion 408.

The body 420 of the adapter 404 also includes a light sensitive element 442 positioned to receive and detect light from the light source 112. The light sensitive element 442 can receive the light from the light source 112 via a light source aperture 440 in the body 420 of the adapter 404, and via one or more mirrors 444. Mirror 444 can be used to divert light to the light sensitive element 442 to provide adequate spacing between the light sensitive element 442 and the camera optical element 426. The light sensitive element 442 can include any suitable electronic detector for measuring incident light, or for acting as a switch in response to incident light, such as: a photoresistive element, a photoresistive switch, or similar device. The light sensitive element 442 can be operably connected, e.g. via a wired or wireless connection, to a secondary light source 450.

The secondary light source 450 includes an independent power supply 452, a control element 454, and a light element 456 such as an LED or comparable light-producing element. The secondary light source 450 can output light into a fiberoptic element 458 for providing light to the illumination element 412 of the endoscope 406 via the port 414. In some embodiments, the secondary light source 450 may be attached directly with the illumination element 412 via the port 414, without the intervening fiberoptic element 458. In alternative embodiments, the secondary light source 450 may be attached with the adapter 404.

Figures 5, 6:
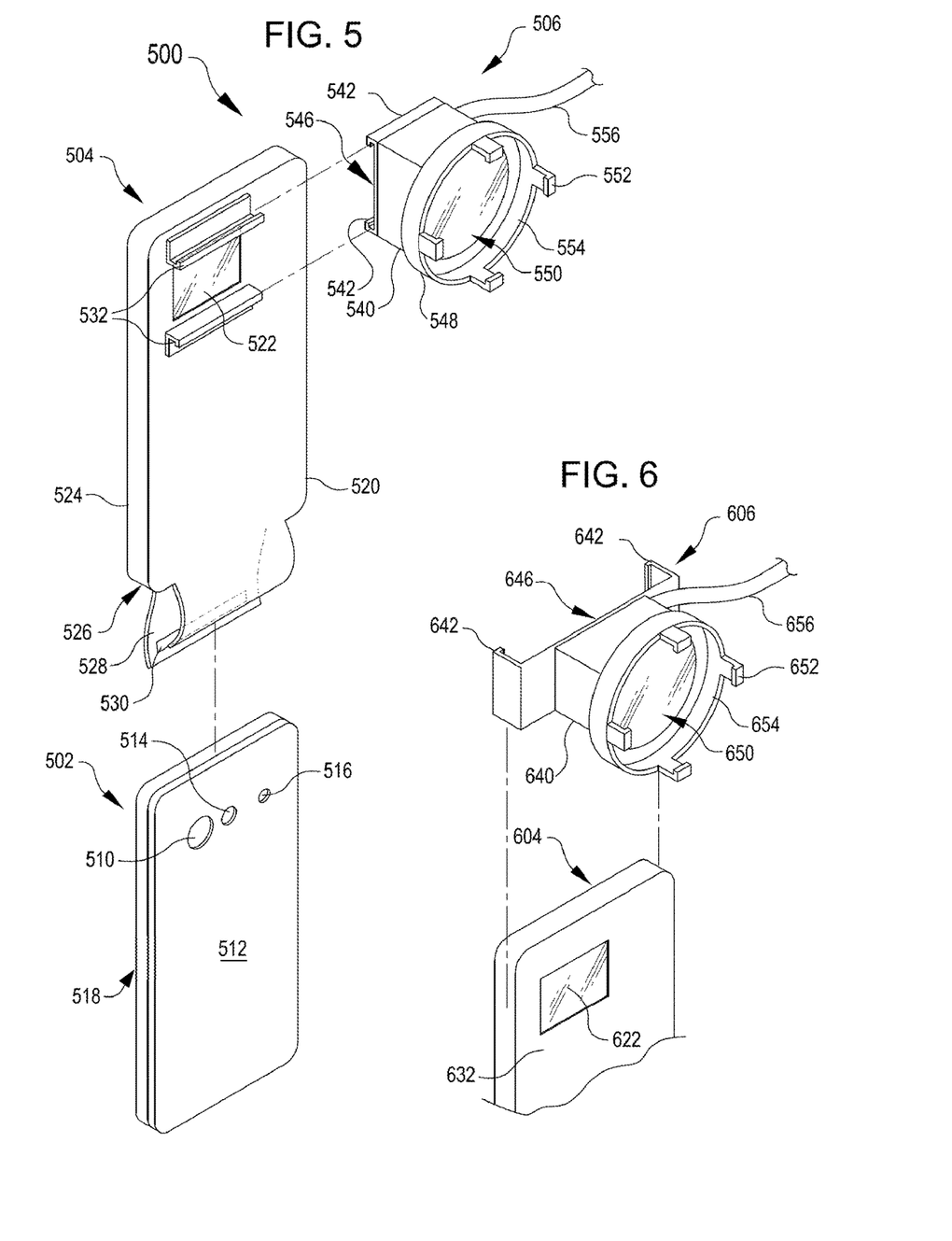
FIG. 5 is a perspective view illustrating an example of a system for protecting an electronic device and for adapting an endoscope with an electronic device.
FIG. 6 is a perspective view illustrating a second example of a system for protecting an electronic device and for adapting an endoscope with an electronic device.

Adapters as described above with respect to FIGS. 1-4 are shown connecting directly with electronic devices. However, adapters can also be configured for connecting over an intervening protective cover, housing, or layer. FIG. 5 is a perspective view illustrating an example of a system 500 including a cover 504 for protecting an electronic device 502 and for adapting an endoscope 506 with the electronic device, in accordance with embodiments. The electronic device 502 is similar to the electronic device 102 described above with respect to FIGS. 1-4, and can include a body 512 housing a camera 510, light source 512, microphone 516 and screen 518. A protective cover 504 is sized to accommodate the electronic device 502. The protective cover includes a body 520 with an opening 526 for receiving the electronic device 502. The opening 526 can include connecting features 528 which can alternatively clip to the electronic device 502, or can wrap around and secure the electronic device by, e.g., a securement element 530 such as an adhesive, magnetic strip, hook-and-loop type securement, or the like. At least a front face 524 of the cover 504 is transparent for allowing a user to view the screen 518 when the electronic device 502 is in the cover. The body 520 of the cover 504 also has an opening 522, which may be fully open or which may include a transparent material, for allowing light to pass unobstructed to and from the camera 510 and light source 514 when the electronic device 502 is inserted in the cover 504. The cover 504 can also include connecting features 532 for connecting with an adapter 506.

The adapter 506 shown in FIG. 5 has similar features to adapters shown above with respect to FIGS. 2-4 including, an adapter body or frame 540, first connecting features 542 for connecting with an electronic device, second connecting features 552 of a receiving element 548 for connecting with an endoscope. The adapter 506 further includes a camera and/or light source aperture 546 for connecting with the camera 510 of the electronic device 502, the light source 514, or both; a light receiving optic 550 in the receiving element 548 for receiving light from an endoscope, and a light source fiberoptic element 556 for diverting light from the light source 514 to an endoscope. The adapter 506 can be attached with the electronic device 502 when the electronic device is inserted in the cover 504 by interfacing the connecting features 532 of the cover with the first connecting features 542 of the adapter, thus aligning the camera and/or light source apertures 546 with the camera 512 and light source 514 of the electronic device. Connecting features 552 can include light-blocking features, such as a shroud 554 for blocking ambient light. An endoscope (not shown) can interface with the receiving element 548 and light source fiberoptic element 556.

An adapter can also interface with a covered electronic device without intervening attachment features of the cover. FIG. 6 is a perspective view illustrating a second example system 600 including a protective cover 604 for protecting an electronic device and for interfacing with an endoscope 606, in accordance with embodiments. Here, the cover 604 includes a cover body 632 and an opening 622, which may be covered with a transparent material or which may be open. The adapter 606 has connecting first connecting features 642 connected with a body or frame 640 of the adapter that align with and wrap around the cover 604. Similar to adapter 506 shown in FIG. 5, adapter 606 can include camera and/or light source apertures that align with the opening 622, as well as a receiving optic 650 for aligning with an endoscope surrounded by one or more second connecting features 652 for connecting the adapter with the endoscope. The connecting features 652 can include a shroud 654 or comparable feature for blocking ambient light. The adapter 606 can include a light source fiberoptic element 656 for directing light to the endoscope.

Figure 7:
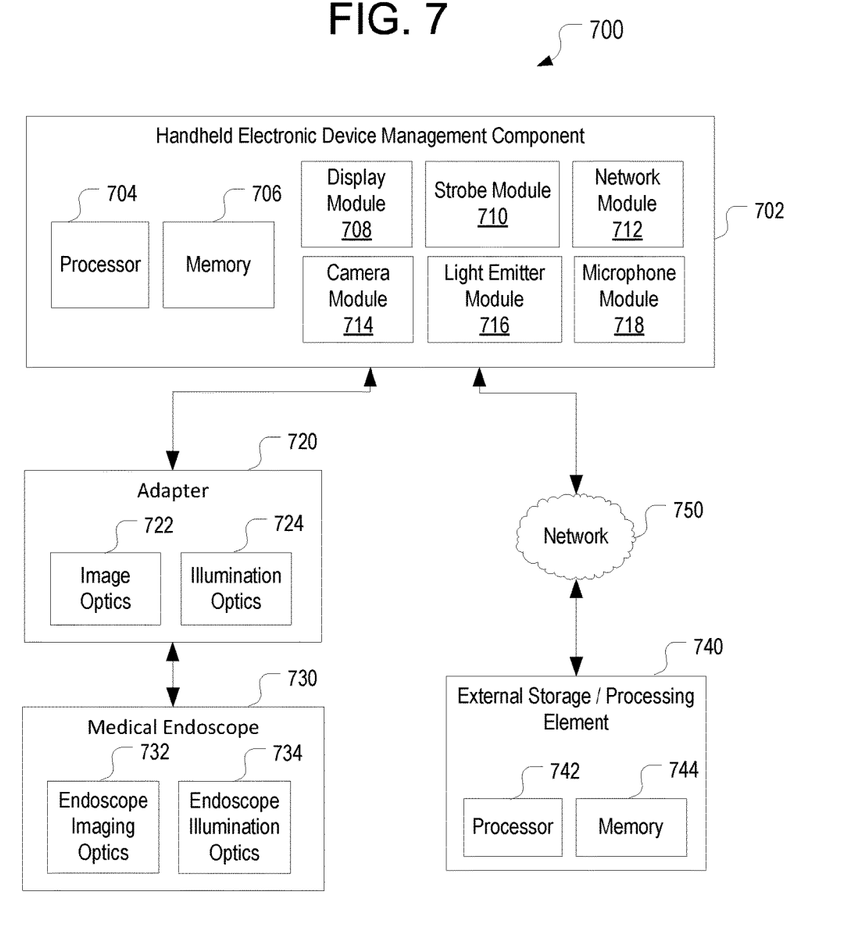
FIG. 7 is a simplified block diagram illustrating a system suitable for conducting endoscopic procedures using an electronic device.

FIG. 7 is a simplified block diagram illustrating an example system 700 suitable for conducting endoscopic procedures using an electronic device in conjunction with an adapter as shown in any of FIGS. 1-6, in accordance with embodiments. The system 700 includes a handheld electronic device management component 702, an adapter 720, and a medical endoscope 730 that are configured to connect together according to the various configurations discussed above with respect to FIGS. 1-6. The system 700 can also include an external storage and/or processing element 740 that connects with the mobile device management component 702 via a network. These components are operable to interact in order to enable a physician to perform various endoscopic procedures.

The handheld electronic device management component 702 includes various components of physical hardware, including a processor 704 and non-transitory memory 706 for storing instructions to control the device; as well as a camera module 714, light emitter module (or light source module) 716, a strobe module 710 for controlling a frequency of cycling the light emitter, a microphone module 718, a display module 708 for displaying information on a screen of the device, and a network module 712 for connecting the electronic device with a network and transferring data to and from the device. Some or all processing and onboard instructions for controlling the above elements may be controlled by an onboard management component of the electronic device 702, such as management component 106 of electronic device 102 shown in FIGS. 1-5. Each respective module of the electronic device management component 702 is operable to control a respective hardware component of an electronic device like the electronic device 102 shown in FIGS. 1-5.

According to various embodiments, the management component 702 can interact and control various components in the system 700. For example, in operation, the management component 702 may interface with image optics 722 and illumination optics 724 of the adapter 720 to cause adjustments to the optical properties of each respective optic, e.g. to increase or decrease magnification. The management component 702 may, in some cases, interface with endoscope imagine and illumination optics 732 and 734, respectively, of a medical endoscope to adjust illumination, image positioning, or magnification. In some cases, the management component 702 can also communicate with an external storage and processing element 740, e.g. via a network 750, in order to upload or download diagnostic information (such as images, video, or patient information) via external processing 742 and memory 744. The system 700 can be used to conduct specific endoscopic procedures, including various forms of stroboscopy.

Figure 8:
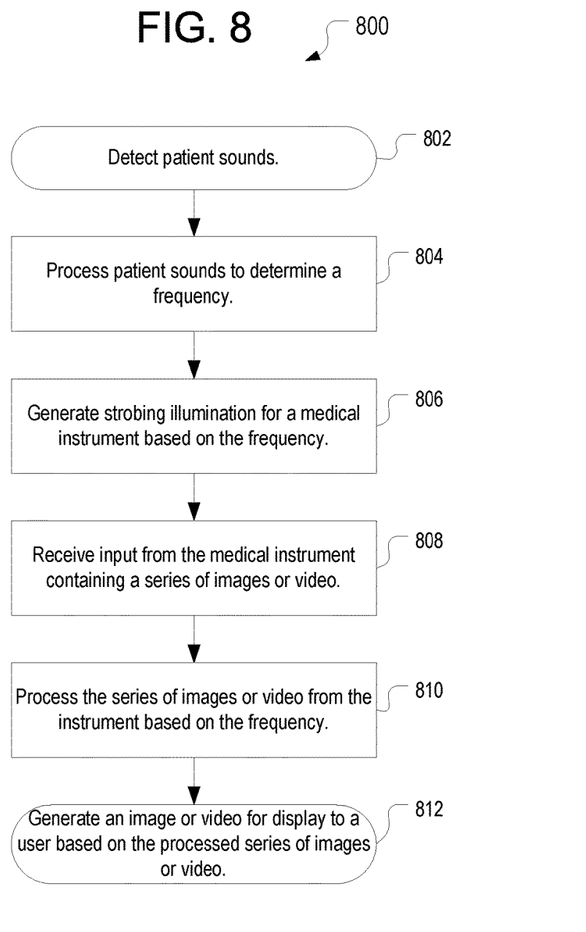
FIG. 8 illustrates a process for conducting a stroboscopic procedure, in accordance with embodiments.

FIG. 8 illustrates a process 800 for conducting a stroboscopic procedure, in accordance with embodiments. Aspects of the process 800 can be performed, in some embodiments, by a system such as system 700 discussed in FIG. 7, and used with components such as a handheld electronic device, adapter, and endoscope like the electronic device 102 shown in FIGS. 1-5 and the adapter and endoscope 104, 106 of FIG. 1, or with the various adapters and endoscopes discussed above with respect to FIGS. 2-6.

In an embodiment, the process 800 includes detecting patient sounds or vocalizations by a microphone and processing those sounds (act 802). The patient sounds or vocalizations can be analyzed to determine a fundamental frequency or other representative frequency (act 804). Then, a strobing illumination frequency can be determined based on the fundamental or representative frequency, and used to cause the system to generate strobing illumination of a medical instrument such as a laryngeal endoscope (act 806). The system can receive input in the form of a series of images or as video from the medical instrument (act 808), which can then be processed to generate diagnostic images or a diagnostic video (act 810). Finally, the series of images or video can be used to generate an image or video for display to a user (act 812).

According to some embodiments, a diagnostic video or image series for display can be generated by processing video taking under strobing light. In some cases, this can include showing the video directly. In some other cases, this can include processing the video to remove frames taken without illumination and/or removing frames taken incidentally with two or more exposures. The effect of using video capture in combination with strobing illumination that matches a fundamental or representative frequency, in the context of laryngeal stroboscopy, is that the captured video appears to view the laryngeal folds in slow-motion during vocalization. However, a similar effect can be achieved by processing video using the fundamental or representative frequency even without using a strobed light source. According to some alternative embodiments, a strobing step (act 806) may be omitted, and a series of images or video may be processed based on the fundamental or representative frequency to produce a set of images or video for diagnostic use.

According to various alternative, embodiments, an endoscopic examination may also be conducted under constant illumination, with or without using patient sounds to process images based on a frequency. In some cases, video may be taken at high framerates to enable high-speed capture, e.g. at 120 frames per second or more.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

What is claimed is:

1. An adapter for coupling a portable electronic device with an endoscope, the adapter comprising:
   a frame;
   a first retention element mounted to the frame and for connecting the adapter with the portable electronic device;
   a camera optical element connected to the frame and arranged to align with a camera of the portable electronic device when the adapter is connected with the portable electronic device, the camera optical element comprising first optics that, when aligned with a viewport of the endoscope, transfers an image from the endoscope to the camera; and
   a light source optical element connected to the frame and comprising second optics that, when aligned with the viewport of the endoscope, cause illumination of a field of view of the endoscope by directing light into the endoscope via the viewport when the adapter is connected with the endoscope.

2. The adapter of claim 1, wherein the camera optical element comprises a spherical lens for magnifying the image for presentation to the camera.

3. The adapter of claim 1, wherein the adapter further comprises:
   a second retention element for connecting the adapter with the endoscope; and
   a viewport optical element configured for directing an image collected from the endoscope to the camera optical element.

4. The adapter of claim 1, further comprising:
   one or more mirrors arranged to align with a light source of the portable electronic device when the adapter is connected with the portable electronic device, the one or more mirrors configured to direct light generated by the light source to the light source optical element in order to cause illumination of the field of view of the endoscope.

5. The adapter of claim 1, further comprising:
   a light sensitive detector configured to detect light generated by a first light source of the portable electronic device; and
   a second light source aligned with the light source optical element and configured to cause illumination of the field of view of the endoscope; wherein
      the light sensitive detector is positioned to receive light from the first light source when the adapter is connected with the portable electronic device, and configured to trigger activation of the second light source in response to receiving light from the first light source.

6. The adapter of claim 5, wherein:
   the second light source comprises a light ring.

7. A system for performing endoscopic procedures, the system comprising:
   an endoscope having an illumination element and a viewport;
   a portable electronic device having a light source, a camera, a microphone, and a display; and an adapter for coupling the portable electronic device with the endoscope, the adapter comprising:
a frame;
a first retention element connected with the frame for connecting the adapter with the portable electronic device;
a second retention element connected with the frame for connecting the adapter with the endoscope;
a camera optic connected with the frame for directing an image from the viewport to the camera when the endoscope and the portable electronic device are connected with the adapter; and
a light source optical element connected with the frame and arranged to align with a first light source of the portable electronic device to cause illumination of a field of view of the endoscope when the adapter is connected with the endoscope; and
a management component comprising a processor and memory containing instructions, the instructions operable to cause the management component to:
receive image data from the camera;
process the received image data to generate video data;
receive an output from the microphone corresponding to a patient's voice;
process the output from the microphone to determine a frequency of the patient's voice;
process the video data based on the frequency to generate diagnostic video data; and
cause the diagnostic video data to be displayed on the display.

8. The system of claim 7, wherein the adapter further comprises: a light sensitive detector connected with the frame and aligned to receive light from the first light source and generate a signal; and a second light source operably connected with the light sensitive detector and coupled with an illumination element of the endoscope so that, when the first light source cycles, the second light source provides strobing illumination to the illumination element of the endoscope at the rate proximate to the frequency.

9. The system of claim 7, wherein the portable electronic device is one of a smartphone, tablet, or portable computer.

10. The system of claim 7, wherein the light source of the portable electronic device comprises at least one LED.

11. The system of claim 7, further comprising:
a protective cover having internal dimensions sized to fit around the portable electronic device between the portable electronic device and the adapter and comprising attachment features for receiving the first retention element of the adapter.

12. A method of conducting endoscopy using a portable electronic device with an endoscope, the method comprising:
with an adapter comprising:
a frame;
a first retention element connected with the frame for connecting the adapter with the portable electronic device;
a second retention element connected with the frame for connecting the adapter with the endoscope;
a camera optical element connected with the frame; and
a light source optical element connected with the frame;
positioning the adapter relative to the portable electronic device via the first retention element to align the camera optical element with a camera of the portable electronic device and to align a first light source of the portable electronic device with the light source optical element;
positioning the adapter with respect to the endoscope via the second retention element to align a viewport of the endoscope with the camera optical element such that light from the viewport enters the camera optical element;
causing illumination of the endoscope via the light source optical element by activating the light source;
receiving an image at the camera from the endoscope via the camera optical element;
processing the received image to generate video data;
receiving an output from a microphone of the portable electronic device corresponding to a patient vocalization;
processing the output to determine a fundamental frequency of the patient vocalization; and
processing the video data based on the fundamental frequency to generate diagnostic video data.

13. The method of claim 12, further comprising:
causing the light source to cycle at a frequency proximate to the fundamental frequency.

14. An adapter for coupling a portable electronic device with an endoscope, the adapter comprising:
a frame;
a first retention element mounted to the frame and for connecting the adapter with the portable electronic device;
a camera optical element connected to the frame and arranged to align with a camera of the portable electronic device when the adapter is connected with the portable electronic device, the camera optical element comprising first optics that, when aligned with a viewport of the endoscope, transfers an image from the endoscope to the camera;
a light sensitive detector configured to detect light generated by a first light source of the portable electronic device when the adapter is coupled with the portable electronic device; and
a second light source connectible with an illumination element of the endoscope and operable to illuminate the endoscope via the illumination element when the second light source is activated, wherein the light sensitive detector is configured to trigger activation of the second light source in response to detecting light from the first light source.

15. The adapter of claim 14, further comprising a fiberoptic element connected with the second light source and connectible with the illumination element of the endoscope.

16. The system of claim 7, wherein the light source optical element comprises an illumination optic that, when aligned with the viewport of the endoscope, causes illumination of the endoscope by directing light into the endoscope via the viewport.

17. The system of claim 7, wherein the adapter further comprises:
a light sensitive detector configured to detect light generated by the first light source when the adapter is coupled with the portable electronic device; and
a second light source operable to illuminate the endoscope when the second light source is activated, wherein the light sensitive detector is configured to trigger activation of the second light source in response to detecting light from the first light source.

18. The system of claim 17, wherein the second light source is connectible with an illumination element of the endoscope.

19. The system of claim 17, wherein the second light source is configured to illuminate the endoscope by directing light into the endoscope via the viewport.

20. The method of claim 12, wherein the adapter further comprises:
- a light sensitive detector; and
- a second light source positioned to illuminate the endoscope and operably connected with the light sensitive detector, the method further comprising:
    - causing illumination of the endoscope by activating the first light source to cause activation of the second light source.

21. The method of claim 12, further comprising uploading the diagnostic video data, via a network, to an external storage device.

* * * * *